United States Patent
Broegger et al.

(10) Patent No.: US 12,403,232 B2
(45) Date of Patent: Sep. 2, 2025

(54) EXTRACORPOREAL BLOOD TREATMENT MACHINE COMPRISING A POKA-YOKE FOR A PRESSURE SENSOR

(71) Applicant: B. Braun Avitum AG, Melsungen (DE)

(72) Inventors: Sebastian Broegger, Knuellwald (DE); Michael Ochse, Melsungen (DE); Kai-Uwe Ritter, Melsungen (DE); Thorsten Thomas, Schwalmstadt (DE)

(73) Assignee: B. Braun Avitum AG, Melsungen (DE)

( * ) Notice: Subject to any disclaimer, the term of this patent is extended or adjusted under 35 U.S.C. 154(b) by 856 days.

(21) Appl. No.: 17/438,980

(22) PCT Filed: Mar. 19, 2020

(86) PCT No.: PCT/EP2020/057642
§ 371 (c)(1),
(2) Date: Sep. 14, 2021

(87) PCT Pub. No.: WO2020/188040
PCT Pub. Date: Sep. 24, 2020

(65) Prior Publication Data
US 2022/0152285 A1    May 19, 2022

(30) Foreign Application Priority Data
Mar. 19, 2019    (DE) .................... 10 2019 107 031.7

(51) Int. Cl.
*G01L 19/00*    (2006.01)
*A61M 1/26*    (2006.01)
*A61M 1/36*    (2006.01)

(52) U.S. Cl.
CPC .......... *A61M 1/3639* (2013.01); *A61M 1/267* (2014.02); *A61M 1/3638* (2014.02); *G01L 19/0007* (2013.01)

(58) Field of Classification Search
None
See application file for complete search history.

(56) References Cited

U.S. PATENT DOCUMENTS

| 5,895,571 A | 4/1999 | Utterberg |
| 9,233,199 B2 | 1/2016 | Krause et al. |
| | (Continued) | |

FOREIGN PATENT DOCUMENTS

| CN | 105874313 A | 8/2016 |
| CN | 105879137 A | 8/2016 |
| | (Continued) | |

OTHER PUBLICATIONS

Office Action received in Chinese Application No. 202080018942.6 dated Jun. 27, 2023, with translation, 14 pages.
(Continued)

*Primary Examiner* — Alexander A Mercado
(74) *Attorney, Agent, or Firm* — Christopher A. Rothe; CM Law (57) ABSTRACT

An extracorporeal blood treatment machine includes a blood treatment device, a conveying device for conveying blood through the blood treatment device, and a connection mask designed to interchangeably receive a tube set in a predefined arrangement. The tube set has pressure-monitoring lines that branch off from the tube set and can be connected to pressure sensor connections located on the connection mask. The pressure sensor connections are spaced apart and positioned so as to match the tube set such that, when the tube set is mounted in the predefined arrangement on the connection mask, each pressure-monitoring line, owing to its limited length and the predefined arrangement of the associated branch on the blood treatment machine, can be connected exclusively to only one of the pressure sensor
(Continued)

connections. A corresponding tube set is used with the extracorporeal blood treatment machine.

19 Claims, 5 Drawing Sheets

(56) References Cited

U.S. PATENT DOCUMENTS

| | | | |
|---|---|---|---|
| 9,551,625 B2 | 1/2017 | Brugger et al. | |
| 10,973,972 B2 | 4/2021 | Ritter | |
| 11,229,728 B1* | 1/2022 | Barneck | A61M 1/285 |
| 2015/0306299 A1 | 10/2015 | Stuva et al. | |
| 2015/0367062 A1* | 12/2015 | Brugger | A61M 1/365 |
| | | | 210/646 |
| 2016/0245271 A1* | 8/2016 | Schaefer | F04B 49/20 |
| 2018/0161488 A1 | 6/2018 | Becker et al. | |
| 2019/0001041 A1 | 1/2019 | Ritter | |
| 2019/0336673 A1 | 11/2019 | Crnkovich et al. | |
| 2021/0077703 A1* | 3/2021 | Hasegawa | A61M 1/3643 |

FOREIGN PATENT DOCUMENTS

| | | |
|---|---|---|
| DE | 112012002327 T5 | 3/2014 |
| DE | 102013103221 A1 | 10/2014 |
| DE | 102018100568 A1 | 7/2019 |
| EP | 3061473 A1 | 8/2016 |
| JP | 861113461 A | 5/1986 |

OTHER PUBLICATIONS

Search Report received in German Application No. 10 2019 107 031.7 dated Mar. 4, 2020, with translation, 18 pages.

Search Report received in International Application No. PCT/EP2020/057642 dated Jun. 24, 2020, with translation, 7 pages.

YouTube Video: CAJES, Wendy, "Setting up a Haemodialysis Machine Fresenius 5008", uploaded Oct. 23, 2015. URL: https://www.youtube.com/watch?v=6DM-3v0jYd4, screen shots and audio transcript, 11 pages.

* cited by examiner

EXTRACORPOREAL BLOOD TREATMENT MACHINE COMPRISING A POKA-YOKE FOR A PRESSURE SENSOR

CROSS-REFERENCE TO RELATED APPLICATIONS

This application is the United States national phase entry of International Application No. PCT/EP2020/057642, filed Mar. 19, 2020, and claims the benefit of priority of German Application No. 10 2019 107 031.7, filed Mar. 19, 2019. The contents of International Application No. PCT/EP2020/057642 and German Application No. 10 2019 107 031.7 are incorporated by reference herein in their entireties.

FIELD

The present disclosure relates to an extracorporeal blood treatment machine, in particular a dialysis machine, comprising a blood treatment device, in particular a filter cartridge (dialyser), a conveying device for conveying blood through the blood treatment device, and a connection mask. The connection mask is designed to interchangeably receive an adapted tube set in a predefined arrangement on the blood treatment machine. The tube set has at least one blood supply line for supplying blood to the blood treatment unit, a blood return line for returning treated blood from the treatment unit as well as at least two transmission lines. Each of the transmission lines branches off the blood supply line or the blood return line at a branch and can be connected to pressure sensor connections located on the blood treatment machine to transmit pressure from the branches to the corresponding pressure sensor connection. The disclosure further relates to a tube set for use with a dialysis machine.

BACKGROUND

The blood tube lines on extracorporeal treatment machines such as dialysis machines must be pressure-monitored. This serves for being able to set the pressures prevailing there in a physiologically compatible range and to act quickly in the event of critical pressure conditions. For this purpose, branches which are in contact with machine-side pressure sensor connections by means of thin tubes (pressure-monitoring lines or pressure-transmission lines) are provided at the blood tube lines. A pressure-monitoring line of this type may be connected to the tube via a T-piece, for example. Then there is an air cushion between a liquid column present in the pressure-monitoring/pressure-measuring line and the pressure sensor. Said air cushion varies with a change of pressure in the tube (expands or is compressed), which in turn results in a deflection of the pressure sensor.

Typically, for example a dialysis machine comprises a pressure sensor connection for monitoring the arterial negative pressure (PA) and a pressure sensor connection for monitoring the venous pressure (PV).

The pressure sensor connections commonly are close to one another and are disposed in an upper region of the machine (above internal fluid systems and in the vicinity of the residual electronics components). Usually, in known systems or tube sets, the tube lengths of the pressure-monitoring lines have a definite excess length. As a consequence, the pressure-monitoring lines can be connected, during assembly or replacement of a tube set, to a wrong pressure sensor connection of the machine. In order to avoid such interchanging, the pressure sensor connections previously have been labeled.

Such interchanging is detected by the blood treatment machine at best during a self-test, the blood treatment machine then triggering an alarm. As a consequence, an operator must come and eliminate the failure by manually correctly connecting the connectors.

SUMMARY

Therefore, it is the object of the present invention to provide an extracorporeal blood treatment machine with simpler operation and simpler assembly, resp., of an interchangeable tube set.

In accordance with the invention, an extracorporeal blood treatment machine comprising a blood treatment device for treating the blood of a patient, a conveying device for conveying blood through the blood treatment device via an extracorporeal blood circuit, and a connection mask (interface) for the extracorporeal blood circuit is provided. The connection mask is configured to interchangeably receive an adapted tube set in a predefined arrangement on the blood treatment machine. The tube set has at least one blood supply line (arterial tube section) for supplying blood to the blood treatment unit, a blood return line (venous tube section) for returning treated blood from the treatment unit. Thus, the tube set predefines the extracorporeal blood circuit. In addition, the tube set includes at least two pressure-monitoring lines. Each of the pressure-monitoring lines branches off the blood supply line or the blood return line at a branch. Moreover, they can be connected to pressure sensor connections on the machine side disposed on the connection mask and are adapted to transmit pressure from a section of the tube set via the branches to the corresponding pressure sensor connection. The pressure sensor connections are spaced (sufficiently far) from one another and are positioned on the extracorporeal blood treatment machine so as to match the tube set such that, when the tube set is mounted in the predefined arrangement predetermined by the connection mask, each of the pressure-monitoring lines, owing to its limited length and the predefined arrangement of the associated branch on the blood treatment machine, can be connected exclusively to a respective one of the pressure sensor connections. In other words, in a blood treatment machine the distance between two pressure sensor connections (connectors) on the machine front is selected so that a particular effect will result when the tube set is mounted in the predefined arrangement on the connection mask. The distance is selected so that the radius resulting between the start of the pressure-monitoring line and the end of the pressure-monitoring line, when viewed from the associated branch, only permits connection to the desired pressure sensor connection.

In this way, a poka-yoke system for the pressure sensor connections that facilitates the operation of the machine and reduces assembling times for attaching the tube set can be implemented. The afore-described connection mask is configured, for example, by the conveying device and the blood treatment device. They define the position and the orientation of tube set sections and, resp., sections of the extracorporeal blood circuit. The connection mask moreover may include further components such as sensors, occlusion clips, holders for air traps and the like.

Of preference, the blood treatment machine may be a dialysis machine and the blood treatment device may be a dialyser filter cartridge, a hemofiltration cartridge or the like.

According to a preferred aspect, the connection mask may have three pressure sensor connections disposed on the blood treatment machine according to the afore-described poka-yoke system. Especially preferred, the blood treatment machine may include an arterial pressure sensor connection, a venous pressure sensor connection and a dialyser inlet-side pressure sensor connection.

According to a preferred development of this embodiment, the three pressure sensor connections may be arranged to be distributed in triangular form and spaced apart from one another on the connection mask. Accordingly, preferably the edge lengths of the triangle formed in this way (the distance of each pressure sensor connection from the two other pressure sensor connections) may be selected so that they are larger than the tube length of the longest one of the three pressure-monitoring lines of the tube set. Preferably, these edge lengths/distances can be selected in a range from 10 to 100 cm, further preferred from 20 to 50 cm (e.g., at 30 cm). The triangular arrangement enables the limited area available to be properly utilized.

According to a preferred embodiment of the invention, one of the pressure sensor connections can be arranged on the connection mask to be lower, when viewed in the vertical direction of the blood treatment machine, than the at least one other pressure sensor connection. In particular, the pressure sensor connection may be distanced by a distance greater or equal to the length of the associated pressure-monitoring line, preferably by a distance ranging from 20 to 70 cm.

According to a preferred embodiment, one of the pressure sensor connections can be arranged to be lower than the conveying device, when viewed in the vertical direction of the blood treatment machine. In particular, the arterial pressure sensor connection can be arranged in a region close to the input/inlet of the conveying device. Preferably, a distance is less than 30 cm, especially preferred less than 15 cm, from the input of the conveying device.

Preferably, the dialyser inlet-side pressure sensor connection can be arranged in a region close to the output/outlet of the conveying device. Of preference, a distance is less than 30 cm, especially preferred less than 15 cm, from the output of the conveying device.

Preferably, the venous pressure sensor connection may be arranged in an area above a holder for a vent (an air trap) of the connection mask. In this case, a distance of less than 30 cm, especially preferred less than 15 cm, to the output of the conveying device is preferred.

In a preferred configuration of the invention, the conveying device is a tube pump (also referred to flexible tube pump, roller pump or peristaltic pump).

Further preferred, the (all) pressure sensor connections are configured as, preferably identical, connectors, in particular Luer lock connectors, which are preferably configured to be connected to connectors, in particular Luer lock connectors, provided on pressure-monitoring lines. Further preferred, the pressure sensor connections are designed as housing passages with a Luer lock connector on the housing outside.

Another aspect of the invention relates to a tube set for use with an extracorporeal blood treatment machine, in particular according to any one of the afore-mentioned aspects, which can be mounted detachably/interchangeably and in a predefined arrangement on a connection mask of the blood treatment machine. The tube set includes at least a blood supply line for supplying blood to a blood treatment unit, a blood return line for returning treated blood from the treatment unit, a pump section adapted and provided to be inserted into and interact with a conveying device of the extracorporeal blood treatment machine, as well as at least two pressure-monitoring lines each of which branches off the blood supply line or the blood return line at a branch and can be connected to pressure sensor connections arranged on the blood treatment machine to transmit pressure from the branches to a pressure sensor connection. The length of the pressure-monitoring lines and the positioning of the branches (in the longitudinal extension direction of the blood supply line and the blood return line) are adapted such that each of the pressure-monitoring lines, when the tube set is attached to the connection mask in the predefined arrangement, only allows making a connection with one predefined pressure sensor connection out of the number of pressure sensor connections.

In this way, a poka-yoke system for the pressure-monitoring lines that facilitates the operation of the machine and reduces assembling times for attaching the tube set can be implemented.

According to a preferred embodiment of the invention, each of the pressure-monitoring lines may include, at its end remote from the tube set, an identical connector, in particular a Luer lock connector, for connection to the predefined pressure sensor connection. Since a mix-up is excluded already by the adapted tube lengths, the connections for pressure sensors can be kept identical to facilitate manufacture.

In accordance with a further preferred aspect, the pump section can be configured in the blood supply line and the blood supply line can have, upstream of the pump section in the conveying direction, an arterial branch from which an arterial pressure-monitoring line connectable to an arterial pressure sensor connection of the dialysis machine branches off.

In accordance with a further preferred aspect, the dialyser inlet-side branch can be arranged between the pump section and a connector for connecting the blood supply line to an inlet of the dialyser.

In accordance with a further preferred aspect, the blood return line may include, arranged between a connector for connection to an outlet of the dialyser and an air trap, a venous branch from which a venous pressure-monitoring line connectable to a venous pressure sensor connection of the dialysis machine branches off.

In accordance with a preferred embodiment, at least one of the branches can be inserted in a tube section as a separate branching element, i.e., does not branch off a vent or a comparable component. In particular, all branches can be inserted, as such a separate branching element, in a tube section. This enables the arrangement of the branches to be designed more flexibly.

Preferably, all pressure-monitoring tubes can be configured to have a tube length of less than 100 cm. Especially preferred, pressure-monitoring tubes can be configured in a length range from 10 to 50 cm.

According to a preferred embodiment of the invention, at least one of the branches can be configured as a (separate) branching element having a pressure oscillating diaphragm (in short: POD). A POD is a branching element that fluidically seals the branch by means of a diaphragm and, resp., separates the branch from the extracorporeal blood circuit, but permits transmission of pressure via the flexibility of the diaphragm. In particular, all branches may be configured as branching elements having PODs of this type.

In accordance with another aspect of the invention, the at least one branch can be branched off at a predefined angle, especially an angle between 45° and 90°, relative to the associated tube section of the blood supply line or the blood return line. Of preference, this can be designed so that, when the tube set is mounted in the predetermined arrangement on the connection mask, the branch is oriented substantially toward the associated pressure sensor connection on the blood treatment machine. Preferably, the associated pressure sensor connection can be located, when viewed from the branching direction of the branch, in an angular range/cone of ±90°, preferably ±45°, especially preferred ±15°. In this way, already the orientation of the branch for the pressure-monitoring lines can assist the user in correctly connecting to the pressure sensor connections.

According to a further preferred aspect, the (all) pressure-monitoring lines include, at their end remote from the branch, preferably identical, connectors, in particular Luer lock connectors, which are preferably arranged and, resp., prepared to be connected to the pressure sensor connections.

Another aspect of the invention relates to a system of an extracorporeal blood treatment machine and a tube set which are adapted to each other according to one or more out of the aspects described above for the individual components.

In particular, the invention thus also relates to a system of an extracorporeal blood treatment machine, particularly as above-described, and to a tube set that can be mounted detachably and, resp., exchangeably and in a predefined arrangement on the blood treatment machine, especially as above-described, wherein the extracorporeal blood treatment machine, particularly dialysis machine, comprises a blood treatment device, particularly dialyser filter cartridge, a conveying device for conveying blood through the blood treatment device, and a connection mask on which pressure sensor connections are disposed, wherein the tube set comprises at least one blood supply line for supplying blood to the blood treatment device, one blood return line for returning treated blood from the blood treatment device, one pump section adapted and provided to be inserted into the conveying device of the extracorporeal blood treatment machine, as well as at least two pressure-monitoring lines each of which branches off the blood supply line or the blood return line at a branch, wherein the pressure-monitoring lines can be connected to the pressure sensor connections to transmit pressure from the branches to the corresponding pressure sensor connection, and wherein the pressure sensor connections are spaced apart from one another and are positioned on the extracorporeal blood treatment machine so as to match the tube set, and the length of the pressure-monitoring lines as well as the positioning of the branches are adapted such that, when the tube set is mounted in the predefined arrangement on the connection mask, each pressure-monitoring line, owing to its limited length and the predefined arrangement of the associated branch on the blood treatment machine, can be connected exclusively to a respective one out of the pressure sensor connections.

According to one aspect of such system, the pressure-monitoring tube lengths and the position of the branches in the arrangement of the tube set fastened to the connection mask may be selected such that the pressure-monitoring tube just reaches the predefined pressure sensor connection plus a certain oversize facilitating better handling. Of preference, said oversize may be selected to be less than 20 cm, especially less than 10 cm, particularly preferred less than 5 cm.

BRIEF DESCRIPTION OF THE DRAWING FIGURES

In the following, the present invention will be described on the basis of a preferred embodiment illustrated in the Figures.

DETAILED DESCRIPTION

Figure 1:
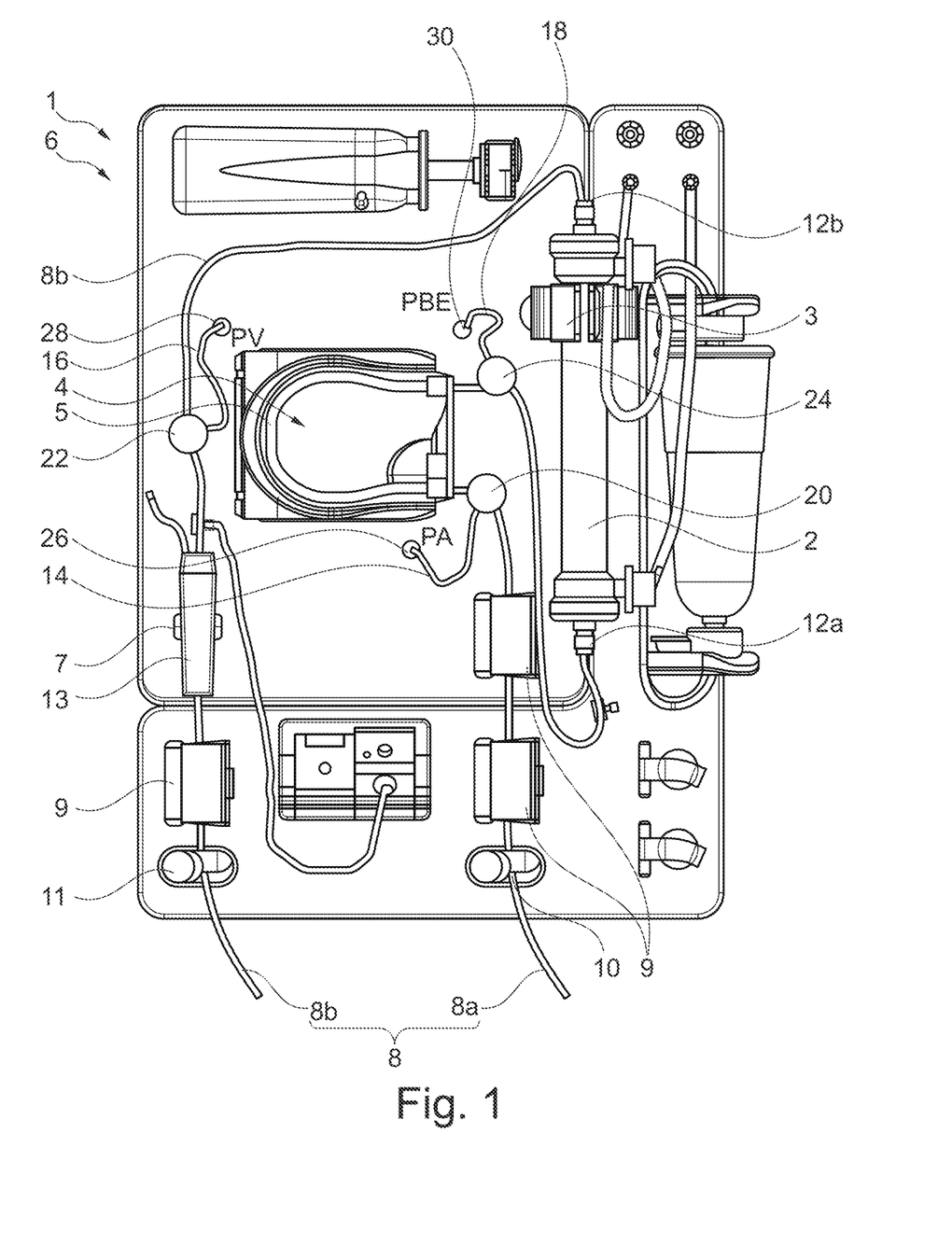
FIG. 1 is a representation for illustrating a system design according to a first embodiment of the present disclosure.

FIG. 1 schematically illustrates a dialysis machine 1 according to a preferred embodiment of the invention in a front view. The dialysis machine 1 includes at its housing front shown in FIG. 1 a blood treatment device 2 (a dialyser in this case) that is interchangeably held at a predefined position and orientation by a holder 3 (in this case a dialyser holder). On the housing front, a conveying device 4 and, resp., a flexible tube pump/peristaltic pump is additionally provided which is configured to pump blood via an extracorporeal blood circuit through the dialyser 2. Said extracorporeal blood circuit is formed by a tube set 8 (disposable article) interchangeably held on a connection mask/connection structure 6 of the dialysis machine. The connection mask 6 is formed by different components on the housing front of the dialysis machine 1 which are specifically adapted to the tube set 8 and by means of which the tube set 8 can be detachably arranged on the housing front in a defined manner so that it can be connected and, resp., operatively connected with the conveying device 4 and the dialyser 2. The conveying device 4 (flexible tube pump) may be regarded as part of the connection mask 6, as, when the tube set 8 is inserted, the position of a pump section 5 of the tube set 8 is determined. The pump section 5 is a tube section designed to be reinforced for the cyclic load by the conveying device 4. Further components of the connection mask 6 are, inter alia, the (dialyser) holder 3, a vent holder 7, diverse sensors 9 (such as temperature sensor, hematocrit sensor, air detector or the like), an arterial tube clamp 10 and a venous tube clamp 11. All of these components combined by the term connection mask 6 have in common that sections of the tube set 8 are connected to or inserted into the connection mask 6 for operation, thus causing the components to predefine a characteristic arrangement of the tube set 8 and, resp., the course of the extracorporeal blood circulation on the dialysis machine.

Summing up, the tube set 8 in the preferred embodiment shown in FIG. 1 together with a blood chamber of the dialyser 2 not shown in detail forms an extracorporeal blood circulation through which blood can be circulated by means of the conveying device 4. The tube set 8 and the dialyser 2 are arranged on the connection mask 6 of the dialysis machine 1 that determines a predefined arrangement on the dialysis machine 1. The tube set 8 and the dialyser 2 are configured as interchangeable disposable articles owing to the direct blood contact occurring during a treatment, whereas connection mask components such as the conveying device 4 are fixedly installed in the housing front.

FIG. 1 illustrates the hose set 8 according to the preferred embodiment, as it is disposed in the predefined arrangement on the connection mask 6 of the dialysis machine 1. The tube set 8 can be roughly divided into a blood supply line 8a (or arterial tube section) for supplying blood of a patient to the dialyser 2 and a blood return line 8b (or venous tube section) for returning treated blood from the treatment unit 2 to the patient. The tube set 8 depicted in FIG. 1 further includes an inlet connector 12a for connecting the blood supply line 8a to an inlet of the blood chamber of the dialyser 2, an outlet connector 12b for connecting the blood return line 8b to an outlet of the blood chamber of the dialyser 2 as well as an air trap disposed in the blood return line 8b or, resp., a vent 13 for filtering air bubbles out of the backflowing blood.

In order to ensure the patient safety and optimum operating parameters, the blood-guiding lines of the tube set 8 must be pressure-monitored. For this purpose, pressure-monitoring lines 14, 16, 18 branch off the blood supply line 8a and the blood return line 8b at defined branches 20, 22, 24. Said pressure-monitoring lines 14, 16, 18 are connected to machine-side pressure sensor connections 26, 28, 30 to which pressure sensors disposed inside the dialysis machine and therefore not shown in detail are connected. The pressure sensor connections 26, 28, 30 are configured as housing passages with a Luer lock connector on the housing outside in the preferred embodiment.

In detail, in the arrangement shown in FIG. 1, the blood supply line 8a includes, upstream of the conveying device 4 in the conveying direction (during normal operation), an arterial branch 20 from which an arterial pressure-monitoring line 14 branches off, the arterial pressure-monitoring line 14 being connected to an arterial pressure sensor connection 26 of the dialysis machine 1 and monitoring the negative pressure (PA) at the tube section facing the arterial patient access.

Further, in FIG. 1, the blood supply line 8a includes a dialyser inlet-side branch 24 between the conveying device 4 and the inlet connector 12a for connection to the inlet of the dialyser 2. A dialyser inlet-side pressure-monitoring line 18 branches off the dialyser inlet-side branch 24. Said pressure-monitoring line 18 is connected to a dialyser inlet-side pressure sensor connection 30 of the dialysis machine 1 and monitors the pressure at the dialyser inlet (PBE).

The blood return line in FIG. 1 includes a venous branch 22 from which a venous pressure-monitoring line 16 branches off, the venous pressure-monitoring line 16 being connected to a venous pressure sensor connection 28 of the dialysis machine 1 and monitoring the pressure (PV) at the venous patient access. The venous branch 22 in the shown embodiment is arranged between the outlet connector 12b for connecting the blood return line 8b to an outlet of the blood chamber of the dialyser 2 and the vent 13.

Figure 9:
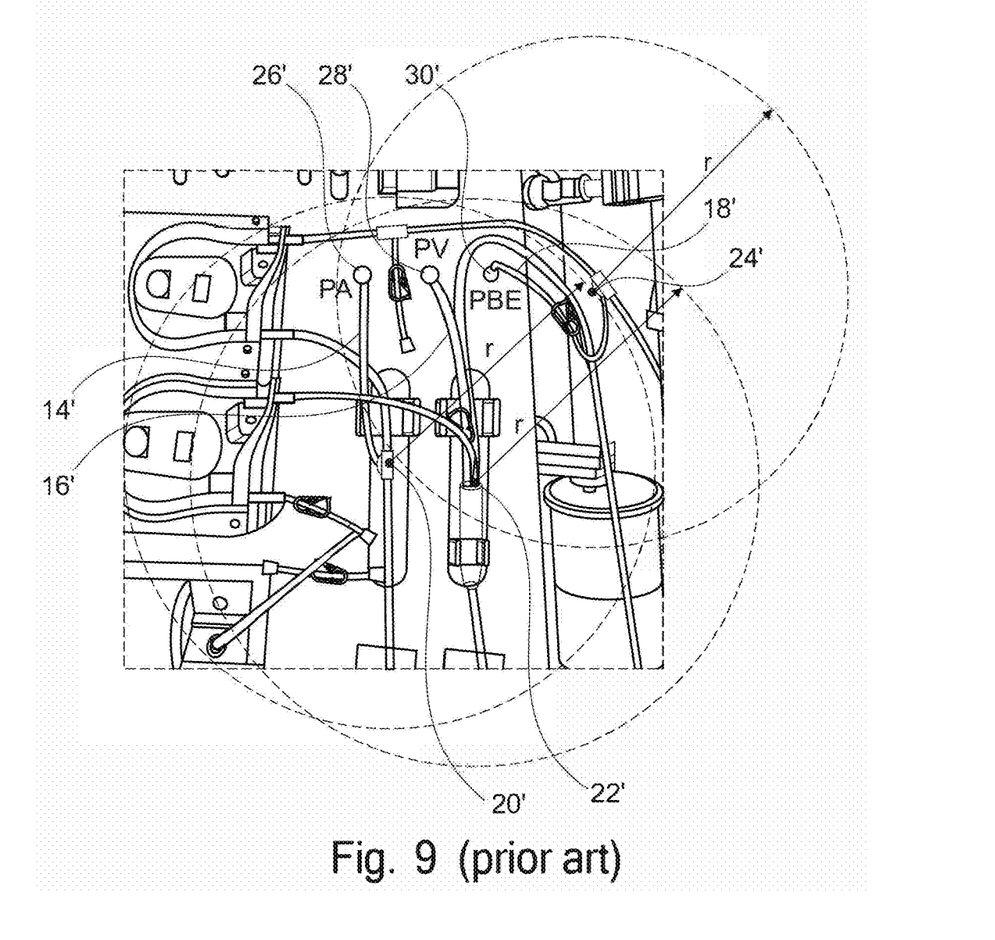
FIG. 9 shows a connection mask of a state-of-the-art dialysis machine with a tube set attached thereto.

In FIG. 9, a cutout of a front of a dialysis machine 1' as known from prior art is exemplified. The dialysis machine 1' largely includes components similar to those of the afore-described dialysis machine 1 according to the preferred embodiment. The pressure-monitoring line 14', 16', 18' in the state of the art is connected, for example, via a T-piece to the tube 8a', 8b' or branches directly off the vent 13' or comparable components having a stationary air volume. Then, between the pressure-monitoring line 14', 16', 18' and the pressure sensor an air cushion is provided the volume of which varies upon pressure variation inside the tube 8a', 8b', which in turn results in a deflection of the pressure sensor. Such pressure measuring method inter alia entails the drawback that the pressure sensor connection 26', 28', 30' must always be arranged above the branch 20', 22', 24' (an air column must be present between the branch and the pressure sensor). Otherwise, there is the risk of the pressure sensor directly contacting the liquid.

As is clearly visible in FIG. 9, the pressure sensor connections 26', 28', 30' are close to one another in an upper region of the connection mask 6. On the one hand, this is based on the fact that the pressure sensor connections 26', 28', 30' must be placed, as afore-explained, above the associated branches 20', 22', 24', and, on the other hand, the majority of the electronic components of the dialysis machine 1' is bundled in the upper region of the interior of the machine. As indicated in FIG. 9 by the radii r, the pressure-monitoring lines 14', 16', 18' are configured to be relatively long due to the comparatively low arrangement of the branches 20', 22', 24'. As a result, the tubes 14', 16', 18' can be interchanged as desired, when they are connected to the pressure sensor connections 26', 28', 30', as all three pressure sensor connections 26', 28', 30' are located inside each circle defined by the radii r.

Figure 2:
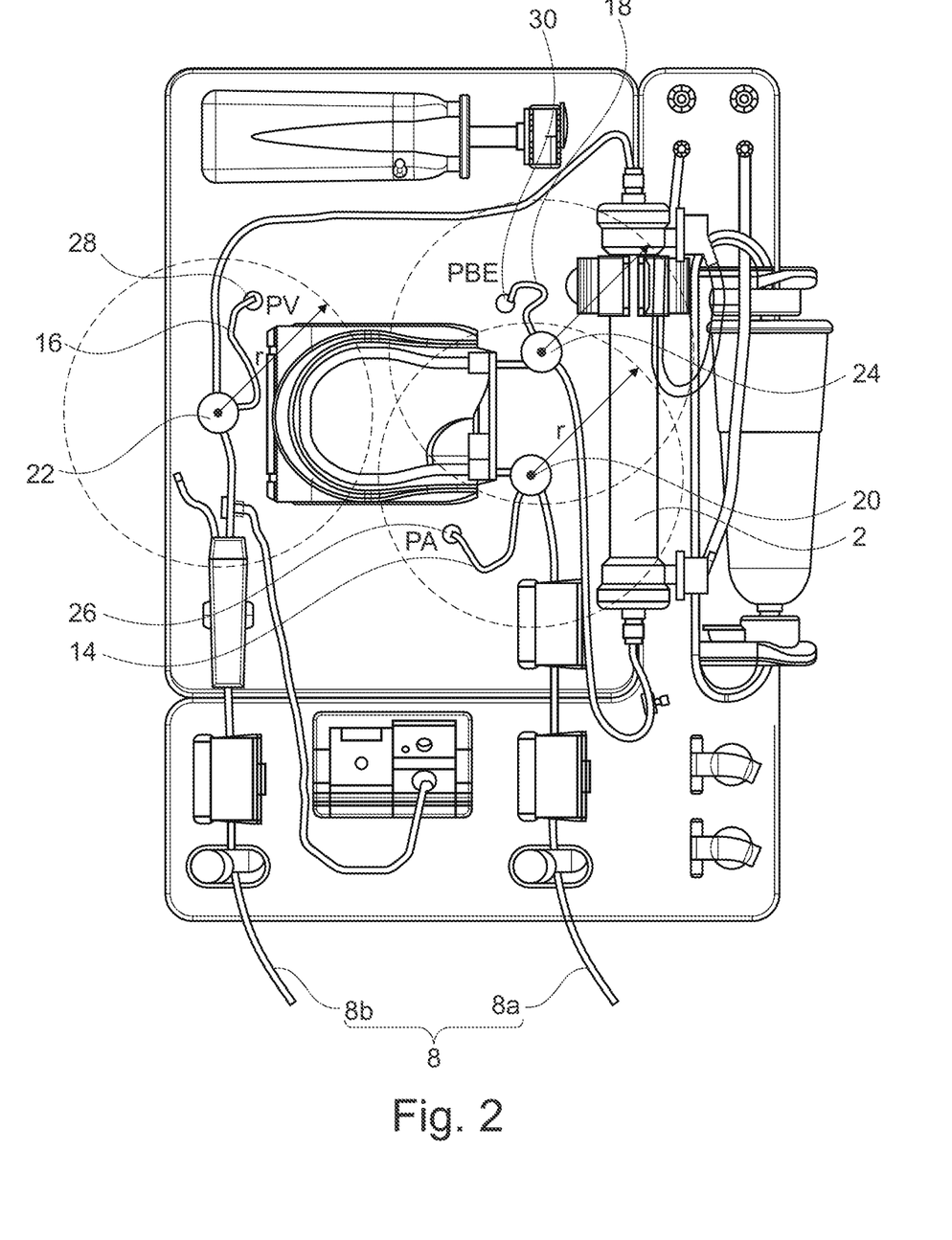
FIG. 2 is a representation for illustrating the system design according to the first embodiment including inserted radii of the pressure-monitoring lines.

In the dialysis machine 1 according to the preferred embodiment, as is best visible from FIG. 2, a poka-yoke system is implemented which drastically facilitates connecting the pressure-monitoring lines 14, 16, 18 to the pressure sensor connections 26, 28, 30. To this end, the connection mask 6 and the tube set 8 are structurally adapted to each other such that, in the predefined arrangement of the tube set 8 predetermined by the connection mask 6, the pressure-monitoring lines 14, 16, 18 cannot be connected to a wrong pressure sensor connection 26, 28, 30. In the shown example, for this purpose the distances between the pressure sensor connections 26, 28, 30 are selected to be sufficiently large and the lengths of the pressure-monitoring lines 14, 16, 18 are selected to be sufficiently small. In addition, the position of the branches 20, 22, 24 in the predefined arrangement of the tube set 8 on the connection mask 6 is selected so that only one respective pressure sensor connection 26, 28, 30 is located within the reach of the pressure-monitoring lines 14, 16, 18 branching off the branch. When the tube set 8 is arranged in the predefined arrangement on the connection mask 6, only the pressure-monitoring lines 14, 16, 18 are therefore allowed to be connected to the respectively correct pressure sensor connection 26, 28, 30. In the preferred embodiment shown in FIG. 2, all pressure-monitoring lines 14, 16, 18 are configured to have the same length. According to an alternative preferred embodiment, the tube lengths of the pressure-monitoring lines 14, 16, 18 can also be clearly different from one another. Due to the predetermined tube length, for each pressure-monitoring line 14, 16, 18 a radius r is resulting within which always exactly one pressure sensor connection 26, 28, 30 can be reached in the arrangement according to the invention. The tube length of the pressure-monitoring lines 14, 16, 18 in the shown example is always selected so that it just reaches the desired pressure sensor connection 26, 28, 30 plus an as short portion as possible to facilitate proper handling.

From FIG. 2 it is clearly evident that the pressure sensor connections 26, 28, 30 are distributed in triangular form on the housing front of the dialysis machine 1. Each of the edge lengths of said triangular form is selected to be larger than the tube length of the pressure-monitoring lines 14, 16, 18 (here 30 cm). The triangular arrangement/distribution of the pressure sensor connections 26, 28, 30 enables of the limited surface area in the region of the connection mask 6 to be properly utilized.

Figure 3:
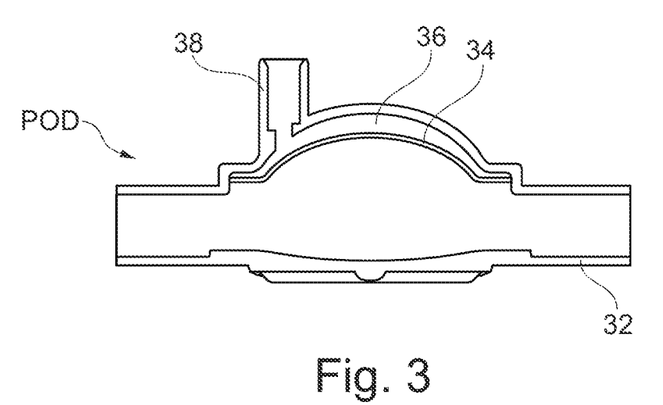
FIG. 3 is a sectional view of a first pressure oscillating diaphragm (POD) connection.

A synergistic effect with the afore-described poka-yoke arrangement results from the use of branches having pressure oscillating diaphragms, also referred to as POD. The pressure-monitoring is not effectuated directly from, e.g., blood to the air cushion, but blood and air are separated from each other via a flexible diaphragm. This structure is clearly visible in FIG. 3 showing an exemplary POD in cross-section. It is evident that a blood line section 32 of the POD insertable as intermediate piece into the tube lines 8a, 8b and an air chamber 36 are separated by a flexible fluid-tight diaphragm 34. A connector 38 serves for connection of a pressure-monitoring line 14, 16, 18 with the air chamber 36. By pressure variation in the blood line section 32 the diaphragm 34 is deflected and said force is transmitted via an air cushion to a pressure sensor that measures the internal tube pressure. This measurement setup offers the advantage that the blood and the air column are uncoupled so that the pressure sensor connection need no longer be arranged above the branch. This results in more freedom of designing the positioning of both the branches 20, 22, 24 (in the mounted state of the tube set 8) and the pressure sensor connections 26, 28, 30. It is a positive side-effect that the blood-air contact is reduced, thus causing the coagulation to be reduced.

By the foregoing use of PODs, in the example shown in FIG. 1 the arterial pressure sensor connection 26 can be placed vertically beneath the conveying device 4 (while the other pressure sensor connections 28, 30 are arranged above the conveying device). This results in a favorable distance from the remaining pressure sensor connections 28, 30.

Figure 4:
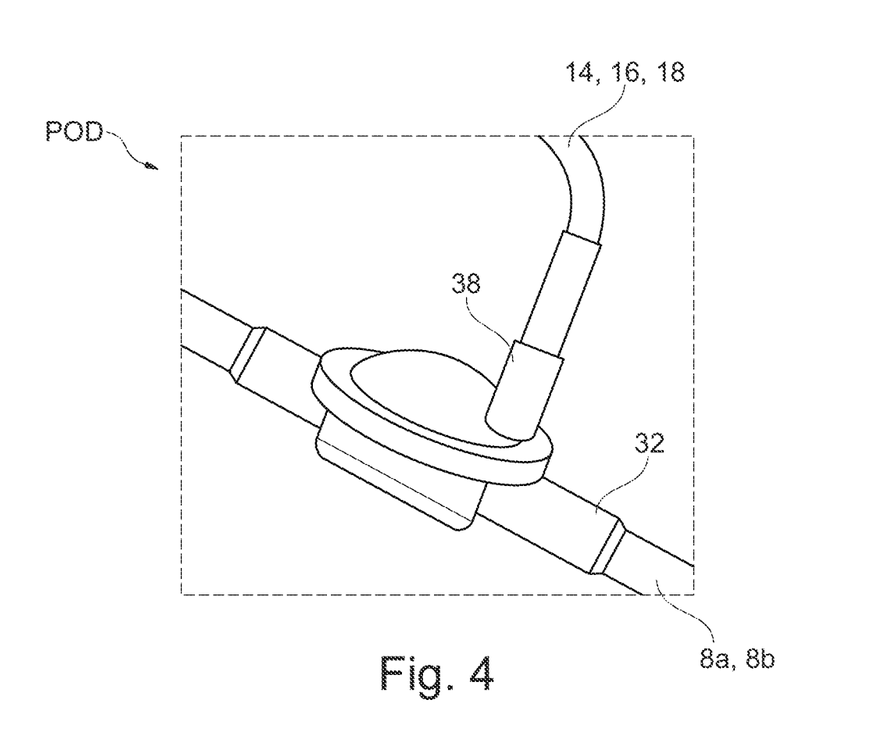
FIG. 4 is a perspective view of the first pressure oscillating diaphragm (POD) connection.
Figure 6:
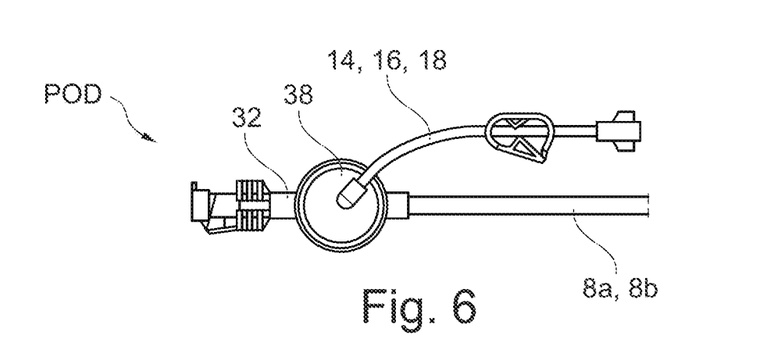
FIG. 6 is a schematic view of the second pressure oscillating diaphragm (POD) connection.
Figure 7:
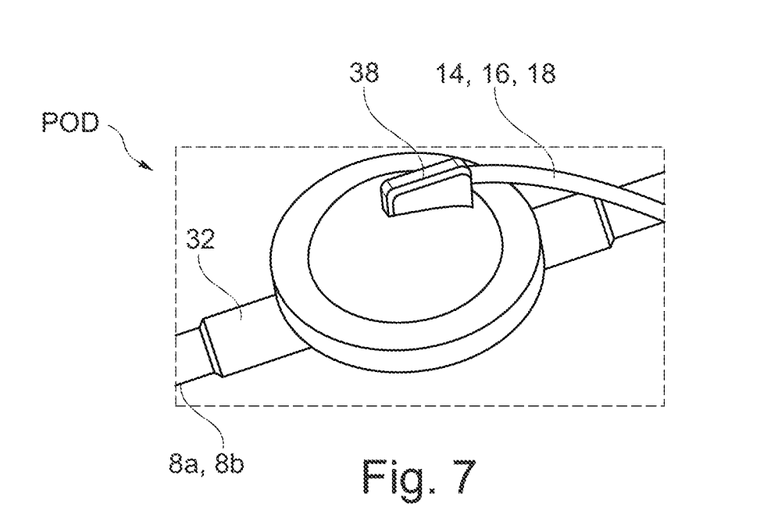
FIG. 7 is a perspective view of a third pressure oscillating diaphragm (POD) connection.

FIGS. 4, 6 and 7 illustrate various embodiments of PODs in which the connector 38 branches off the air chamber 36 in respective different orientations. In commercially available PODs, the connector 38 is usually oriented perpendicularly to the POD circular area and, resp., to the diaphragm 34 (cf. FIG. 4) or extends in parallel to the blood line section 32 (cf. FIG. 7).

In the preferred embodiment of the invention illustrated in FIG. 1, for example, the tube set includes exclusively branches 20, 22, 24 in the form of PODs. In each of said PODs 20, 22, 24, the connector 38 is oriented in parallel to the POD circular area (with the housing front) but at a defined angle (in the top view) with the blood line section 32. Such POD branch is also shown in detail in FIG. 6. In the embodiment shown in FIG. 1, the branching angles of the connectors 38 of the PODs are configured such that, when the tube set 8 is attached to the connection mask in the predefined arrangement, the connectors 38 are already oriented toward the associated pressure sensor connection 26, 28, 30. Thus, the user is supported in mounting the tube set on an intuitive level.

Figure 5:
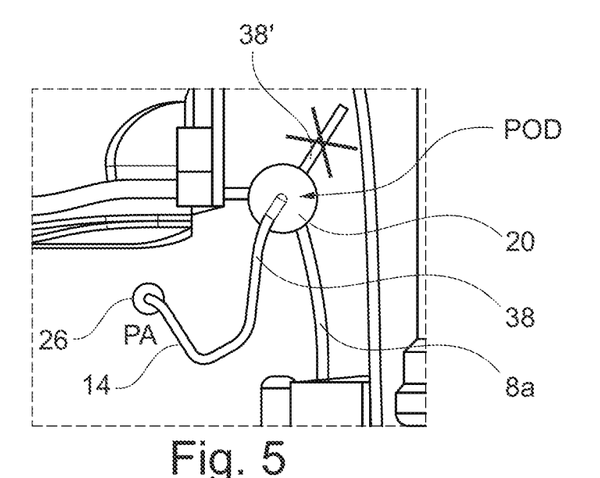
FIG. 5 is a schematic view of a second pressure oscillating diaphragm (POD) connection in the mounted state.

This concept is detailed once again in FIG. 5. As is equally symbolized by the crossed-out connector 38' in FIG. 5, in this way the branches 20, 22, 24 can be prevented in any case from facing opposite to the intended pressure sensor connection 26, 28, 30.

In other words, the orientation of all branches 20, 22, 24 can preferably be chosen so that they deviate by less than 90° (better less than 15°) from a direct line to the intended pressure sensor connection 26, 28, 30.

Figure 8:
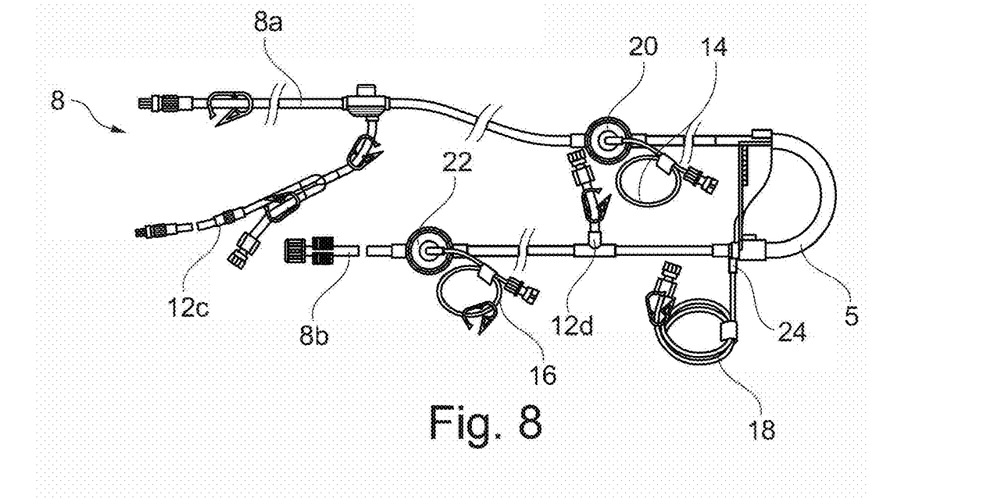
FIG. 8 is a representation of an exemplary tube set according to the present invention.

FIG. 8 illustrates a tube set 8 according to another embodiment of the invention in an isolated representation. The tube set 8 depicted in FIG. 8 includes an arterial branch 20 in the form of a POD and a venous branch 22 in the form of a POD. In the tube set according to FIG. 8, the dialyser inlet-side branch 24 with the associated pressure-monitoring line directly branches off an insert of the pump section 5. In the associated dialysis machine (not shown) the dialyser inlet-side pressure sensor connection 30 is located vertically above the conveying device 4 so that the branch 24 is oriented in the direction thereof. The pressure-monitoring lines 14, 16 branching off the latter have a tube length of 20 cm and a respective Luer lock connector at their free end. The inlet connector 12a for connecting the blood supply line 8a to an inlet of the blood chamber of the dialyser 2, the outlet connector 12b for connecting the blood return line 8b to an outlet of the blood chamber of the dialyser 2 and the vent 13 are hidden in FIG. 8 for reasons of clarity. In the tube set 8 of FIG. 8, additionally a predilution connector 12c is provided in the blood supply line 8a and a predilution connector 12d is provided in the blood return line 8b.

The invention claimed is:

1. A system for extracorporeal blood treatment comprising:
   an extracorporeal blood treatment machine; and
   a tube set that is detachably mountable on the extracorporeal blood treatment machine in a predefined arrangement;
   the extracorporeal blood treatment machine comprising:
      a blood treatment device, a conveying device for conveying blood through the blood treatment device, and a connection mask on which at least two pressure sensor connections are located;
      the at least two pressure sensor connections including a first pressure sensor connection and a second pressure sensor connection;
   the tube set comprising a blood supply line for supplying blood to the blood treatment device, a blood return line for returning treated blood from the blood treatment device, a pump section adapted and provided to be inserted into the conveying device, and at least two pressure-monitoring lines,
   the at least two pressure-monitoring lines including a first pressure-monitoring line and a second pressure-monitoring line,
   the first pressure-monitoring line branching off of the tube set at a first branch, and the second pressure-monitoring line branching off of the tube set at a second branch,
   the first pressure-monitoring line having a first length and being connectable to the first pressure sensor connection to transmit pressure from the first pressure-monitoring line to the first pressure sensor connection,
   the second pressure-monitoring line having a second length and being connectable to the second pressure sensor connection to transmit pressure from the second pressure-monitoring line to the second pressure sensor connection,
   the first and second pressure sensor connections being positioned on the extracorporeal blood treatment machine in a spaced arrangement,
   the first length of the first pressure-monitoring line and the spaced arrangement of the first and second pressure sensor connections being configured so that the first pressure-monitoring line is attachable only to the first pressure sensor connection when the tube set is mounted to the extracorporeal blood treatment machine in the predefined arrangement, and
   the second length of the second pressure-monitoring line and the spaced arrangement of the first and second pressure sensor connections being configured so that the second pressure-monitoring line is attachable only to the second pressure sensor connection when the tube set is mounted to the extracorporeal blood treatment machine in the predefined arrangement; and wherein the first branch is attached at a first connection point to a first tube section of the tube set, and extends from the first connection point away from the first tube section at a predetermined angle relative to the first tube section so that, when the tube set is mounted in the predefined arrangement on the connection mask, the first branch is oriented to extend from the first connection point toward the first pressure sensor connection.

2. The system according to claim 1, wherein the at least two pressure sensor connections comprises the first pressure sensor connection, the second pressure sensor connection and a third pressure sensor connection.

3. The system according to claim 2, wherein the first pressure sensor connection is an arterial pressure sensor connection, the second pressure sensor connection is a blood treatment device inlet-side pressure sensor connection, and the third pressure sensor connection is a venous pressure sensor connection.

4. The system according to claim 2, wherein the first pressure sensor connection, the second pressure sensor connection and the third pressure sensor connection are spaced apart from one another and distributed in a triangular arrangement on the connection mask.

5. The system according to claim 1, wherein one of the at least two pressure sensor connections is arranged to be lower in a vertical direction than another of the at least two pressure sensor connections.

6. The system according to claim 5, wherein said one of the at least two pressure sensor connections is arranged to be lower in the vertical direction than the conveying device.

7. The system according to claim 1, wherein the at least two pressure sensor connections are configured as first connectors arranged to be connected to second connectors provided on the at least two pressure-monitoring lines.

8. The system according to claim 1, wherein the first branch is located upstream of the pump section in a conveying direction, the first pressure sensor connection comprises an arterial pressure sensor connection, the second branch is located between the pump section and a connector piece for connecting the blood supply line to an inlet of the blood treatment device, and the second pressure sensor connection comprises a blood treatment device inlet-side pressure sensor connection.

9. The system according to claim 1, wherein the blood return line includes, between a connector piece for connection to an outlet of the blood treatment device and an air trap, a venous branch from which a venous pressure-monitoring line branches off which can be connected to a venous pressure sensor connection of the extracorporeal blood treatment machine.

10. The system according to claim 1, wherein at least one of the first branch and the second branch is configured as a separate branching element comprising a pressure oscillating diaphragm fluidically sealing said at least one of the first branch and the second branch.

11. The system according to claim 1, wherein the first and second pressure-monitoring lines include connectors designed to be connected to the first and second pressure sensor connections.

12. The system according to claim 1, wherein:
the at least two pressure sensor connections further comprises a third pressure sensor connection, the third pressure sensor connection being positioned on the extracorporeal blood treatment machine in a spaced arrangement with respect to the first pressure sensor connection and the second pressure sensor connection;
at least two pressure-monitoring lines further comprises a third pressure-monitoring line branching off the blood supply line or the blood return line at a third branch;
the third pressure-monitoring line having a third length and being connectable to the third pressure sensor connection to transmit pressure from the third pressure-monitoring line to the third pressure sensor connection;
the third length of the third pressure-monitoring line and the spaced arrangement of the first pressure sensor connection, the second pressure sensor connection and the third pressure sensor connection being configured so that the third pressure-monitoring line is attachable only to the third pressure sensor connection when the tube set is mounted to the extracorporeal blood treatment machine in the predefined arrangement.

13. The system according to claim 1, wherein the first branch is oriented at an angle of ±45° towards the first pressure sensor connection.

14. The system according to claim 1, wherein the first branch is oriented at an angle of ±15° towards the first pressure sensor connection.

15. The system according to claim 1, wherein the first branch comprises a connector extending from a housing forming a portion of the tube set.

16. The system according to claim 15, wherein the housing comprises a pressure oscillating diaphragm.

17. The system according to claim 1, wherein the second branch is attached at a second connection point to a second tube section of the tube set, and extends from the second connection point away from the second tube section at a predetermined angle relative to the second tube section so that, when the tube set is mounted in the predefined arrangement on the connection mask, the second branch is oriented to extend from the second connection point toward the second pressure sensor connection.

18. The system according to claim 17, wherein the first branch extends from the blood supply line, and the second branch extends from the blood supply line.

19. The system according to claim 17, wherein the first branch extends from the blood supply line, and the second branch extends from the blood return line.

* * * * *